(12) United States Patent
Goerlach-Doht et al.

(10) Patent No.: US 9,334,416 B2
(45) Date of Patent: *May 10, 2016

(54) PROCESS FOR PRODUCING CELLULOSE DERIVATIVES OF HIGH BULK DENSITY, GOOD FLOWABILITY AND IMPROVED DISPERSIBILITY IN COLD WATER

(75) Inventors: Yvonne M. Goerlach-Doht, Rosengarten (DE); Juergen Hermanns, Nottensdorf (DE); Peter E. Pierini, Lake Jackson, TX (US); Marco Grossstueck, Walsrode (DE); Michael Schreck, Walsrode (DE)

(73) Assignee: Dow Global Technologies LLC

( * ) Notice: Subject to any disclaimer, the term of this patent is extended or adjusted under 35 U.S.C. 154(b) by 56 days.

This patent is subject to a terminal disclaimer.

(21) Appl. No.: 14/009,442

(22) PCT Filed: Mar. 29, 2012

(86) PCT No.: PCT/US2012/031112
§ 371 (c)(1),
(2), (4) Date: Oct. 2, 2013

(87) PCT Pub. No.: WO2012/138533
PCT Pub. Date: Oct. 11, 2012

(65) Prior Publication Data
US 2014/0013999 A1    Jan. 16, 2014

Related U.S. Application Data

(60) Provisional application No. 61/472,227, filed on Apr. 6, 2011.

(51) Int. Cl.
C08B 11/193 (2006.01)
A61K 47/38 (2006.01)
(Continued)

(52) U.S. Cl.
CPC ............. *C09D 101/28* (2013.01); *A61K 47/38* (2013.01); *C08B 11/08* (2013.01); *C08B 11/20* (2013.01);
(Continued)

(58) Field of Classification Search
USPC ............. 106/163.01, 172.1; 264/301; 536/91
See application file for complete search history.

(56) References Cited

U.S. PATENT DOCUMENTS

| 2,331,864 A | 10/1943 | Swinehart et al. |
| 4,091,205 A | 5/1978 | Onda et al. |

(Continued)

FOREIGN PATENT DOCUMENTS

| EP | 0370447 | 5/1990 |
| EP | 0714656 | 6/1996 |

(Continued)

OTHER PUBLICATIONS

Houben-Weyl, Methoden Der Organischen Chemie, Erweiterungs-UndFolgebande zur vierten auflage.
(Continued)

*Primary Examiner* — Kaj K Olsen
*Assistant Examiner* — Alexander Polyansky

(57) ABSTRACT

A particulate cellulose derivative is obtained in a process of grinding and drying a moist cellulose derivative which comprises the steps of A) providing a cellulose derivative having a moisture content of from 60 to 95 percent, based on the total weight of the moist cellulose derivative, B) grinding and partially drying the moist cellulose derivative in a gas-swept impact mill; and C) contacting the ground and partially dried cellulose derivative with an additional amount of a drying gas outside the gas-swept impact mill. The obtained particulate cellulose derivative has a high untapped bulk density and a good flowability.

12 Claims, 1 Drawing Sheet

(51) Int. Cl.
  *C09D 101/28* (2006.01)
  *C08B 11/20* (2006.01)
  *C08J 3/05* (2006.01)
  *C08J 3/12* (2006.01)
  *C08B 11/08* (2006.01)
  *C08B 11/22* (2006.01)
  *A61K 9/48* (2006.01)

(52) U.S. Cl.
  CPC . *C08B 11/22* (2013.01); *C08J 3/05* (2013.01); *C08J 3/124* (2013.01); *C08J 2301/26* (2013.01); *C08J 2301/28* (2013.01)

(56) References Cited

U.S. PATENT DOCUMENTS

| | | | |
|---|---|---|---|
| 4,979,681 A * | 12/1990 | Donges et al. | 241/17 |
| 6,320,043 B1 | 11/2001 | Weber et al. | |
| 6,410,050 B1 | 6/2002 | Yang | |
| 7,361,753 B2 | 4/2008 | Hammes et al. | |
| 2001/0025101 A1* | 9/2001 | Schlesiger et al. | 536/30 |
| 2001/0034441 A1 | 10/2001 | Schlesiger et al. | |
| 2003/0122003 A1 | 7/2003 | Schlesiger et al. | |
| 2006/0155013 A1* | 7/2006 | Bumm et al. | 524/34 |
| 2007/0175361 A1 | 8/2007 | Bonney et al. | |
| 2008/0039621 A1 | 2/2008 | Maruyama et al. | |
| 2008/0207893 A1* | 8/2008 | Berglund et al. | 536/86 |

FOREIGN PATENT DOCUMENTS

| | | |
|---|---|---|
| EP | 0824107 | 2/1998 |
| EP | 0954536 | 11/1999 |
| EP | 1099709 | 5/2001 |
| EP | 1127895 | 8/2001 |
| GB | 804306 | 8/1962 |
| GB | 2262527 | 6/1993 |
| WO | 9600748 | 1/1996 |
| WO | 2008050209 | 5/2008 |
| WO | 2008067930 | 6/2008 |
| WO | 2012015400 | 2/2012 |

OTHER PUBLICATIONS

Ullmann's Encyclopedia of Industrial Chemistry, Fifth, CompletelyRevised Edition, vol. A5: Cancer Chemotherapy to Cheamic Colorants, 1986.

Witt, Partec, Current Limits of Particle Size and Shape Analysis with High Speed Image Analysis, 2007.

* cited by examiner

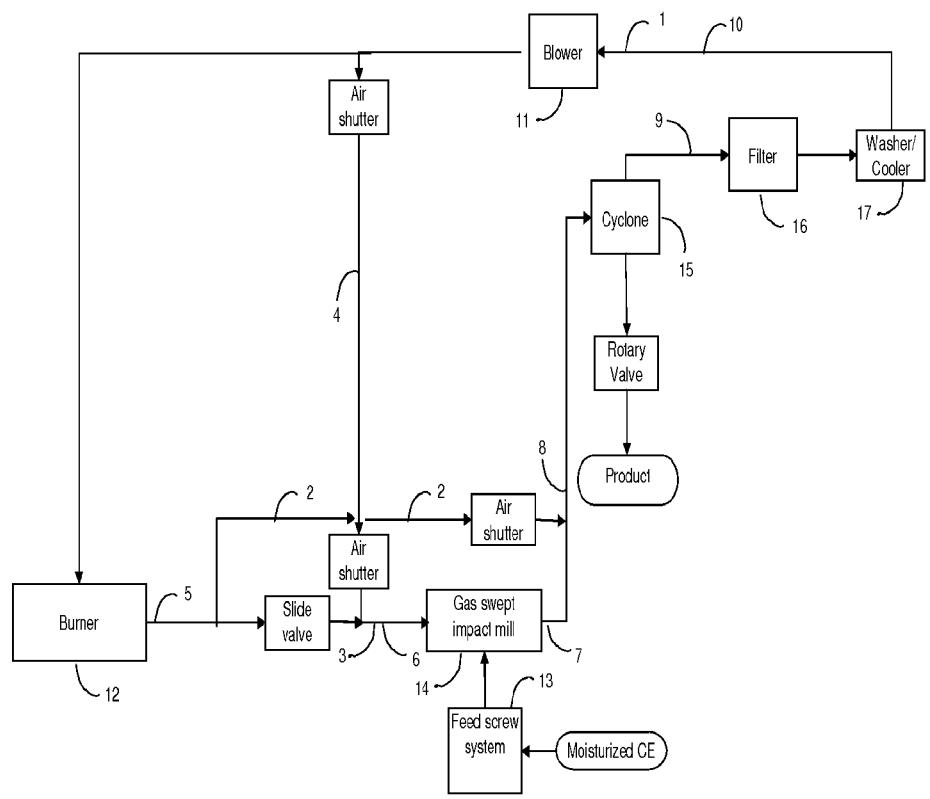

PROCESS FOR PRODUCING CELLULOSE DERIVATIVES OF HIGH BULK DENSITY, GOOD FLOWABILITY AND IMPROVED DISPERSIBILITY IN COLD WATER

CROSS REFERENCE TO RELATED APPLICATIONS

This application is a 35 USC §371 national phase filing of PCT/US12/031112 filed Mar. 29, 2012, which claims the benefit of Application No. 61/472,227, filed Apr. 6, 2011.

FIELD

The present invention relates to a particulate cellulose derivative of high bulk density and good flowability and to a process for producing a particulate cellulose derivative of high bulk density, good flowability and improved dispersibility in cold water.

Cellulose derivatives are industrially important and are used in a large variety of technology areas and in many different end-use applications, for example in the personal care or pharmaceutical industry, in agricultural applications, and in the building or oil industry. Their preparation, properties and applications are described, for example, in Ullmann's Encyclopedia of Industrial Chemistry, 5th Edition, (1986), Volume A5, pages 461-488, VCH Verlagsgesellschaft, Weinheim or in "Methoden der organischen Chemie" (methods of organic chemistry), 4th Edition (1987), Volume E20, Makromolekulare Stoffe, Part Volume 3, pages 2048-2076, Georg Thieme Verlag, Stuttgart.

Water-soluble cellulose derivatives have found widespread use. These water-soluble cellulose derivatives are conveniently supplied as a particulate dry material that is then dissolved in water for the desired end use of such water-soluble cellulose derivatives.

It is desirable that the cellulose derivatives have a reasonably high bulk density and a good flowability to facilitate transportation and handling of the cellulose derivatives.

Unfortunately, many water-soluble cellulose derivatives are not dispersible in cold water. Non-dispersibility is due to the large surface area and fibrous nature of the cellulose derivatives. The large surface area leads to the outside particles of the cellulose derivatives being hydrated before the inside of the particles when added to water. A gelatinous membrane of hydrated outside particles is thus formed around the inside particles, shielding the inside particles from complete hydration. The first particles that come into contact with water immediately swell and stick to each other, forming a gel-like barrier that shields the remaining particles from hydration. This gel-blocking behavior of water-soluble cellulose derivatives is a considerable drawback for those applications that comprise the solution of the particulate water-soluble cellulose derivatives such as cellulose ethers in aqueous systems. The gel blocking behavior is visible as the formation of "lumps" which require a long time for complete dissolution. To overcome this gel blocking behavior or the formation of lumps the cellulose derivatives are dispersed in hot water, typically above about 80° C. During agitation the dispersion is cooled and dissolution of the cellulose derivative takes place. At a specific temperature the cellulose derivative starts to dissolve and to build up viscosity. This so-called hot/cold water dissolution technique takes advantage of the fact that water-soluble cellulose derivatives such as cellulose ethers are generally insoluble in hot water and soluble in cold water, depending on the type and degree of substitution. Unfortunately, this hot/cold water dissolution technique is quite time-consuming for those who have to prepare aqueous solutions of the cellulose derivatives. Accordingly, the skilled artisans have intensely searched for ways of making cellulose derivatives dispersible in cold water, i.e., water below, at or only slightly above room temperature, without the formation of a substantial amount of lumps. Various methods have been suggested, such as temporarily cross-linking with a dialdehyde such as glyoxal or treatment with surfactants. However, these methods are not desirable for cellulose ethers in pharmaceutical or food applications. Other methods describe the usage of tensides (surfactants) added to the cellulose during production, see U.S. Pat. No. 7,361,753 B2, or surface coating using additives such as a salts, sugars, surfactants or low molecular weight water soluble polymers during the drying process, see US Patent Application Publication No. 2007/0175361.

British Patent Specification GB 804,306 discloses a process wherein a wet mixture comprising from 2 to 35 percent of fibrous cold-water soluble cellulose ether and from 98 to 65 percent by weight of hot water is formed at a temperature above the gel point of the cellulose ether, the mixture is cooled below its gel point, e.g. to 20° C., until the fibrous structure substantially disappears and the mass becomes transparent, the temperature is raised to a point above which syneresis occurs, e.g. to 90° C., then the mixture is maintained at a point above the gel point until dry, e.g. in an oven, and the dried product is reduced to the desired particle size, e.g. such that 92% or more of the cellulose ether pass through a 42 mesh screen (corresponding to an opening of 354 micrometers). However, such process has been too time and energy intense to be used on large scale.

U.S. Pat. No. 2,331,864 discloses a method of treating a fibrous cold-water soluble cellulose ether to improve its rate of solution in cold water. In the disclosed process the water content of the water-wet fibrous cellulose ether is set to a value of from 72 to 88 percent by weight at a temperature above 50° C., preferably above 70° C., by making a uniform slurry of from 1 to 5 weight percent of methylcellulose in hot water and subsequent removal of the excess water, e.g., by pressing or by filtering under vacuum. The moist mass is cooled to a temperature below 50° C., preferably to 5-23° C. The cooled mass is allowed to age until the desired degree of gel formation has taken place, i.e., until the mass becomes translucent and substantially without visible fibrous structure. Then the mass is immediately dried at a temperature above 50° C. by spreading it on trays and blowing a stream of hot air over it to a moisture content of less than 15 percent. The dried product is ground. Product of 60 to 100 mesh fineness or finer is obtained and is said to be a free-flowing, non-caking powder which dissolves readily when simply stirred with cold water. However, the disclosed process involves many steps and is time-consuming. Moreover, the wet mass of 72-88 percent water content appears to be sticky and hard to homogeneously handle as described in U.S. Pat. No. 2,331,864 on a large scale. Plugging issues during the described partial drying on trays will lead to inoperability in a manufacturing process because big lump formation will block the transport of the material.

The International Patent Application WO 96/00748 discloses a process for the extrusion of an aqueous hydrated cellulose ether having a water content of 40-75% and a temperature below 40° C. through a plurality of orifices of cross-sectional area of 0.0075-1 $mm^2$ to form an elongated cellulose ether extrudate in the shape of strands, drying and then cutting the elongated cellulose ether extrudate to the desired length. After having dried the cellulose ether to a moisture content of about 25 percent, cutting can be conducted in an air-swept impact mill wherein hot air is blown across the mill Cellulose ether particles of good dispersibility in water are achieved, but unfortunately the process is not used on large scale due to the high equipment costs when extruding the aqueous hydrated cellulose ether into strands and subsequently cutting them in an air-swept impact mill.

One aspect of the present invention is to provide cellulose derivatives which have a good flowability in combination with a reasonably high untapped bulk density.

A preferred object of the present invention is to provide cellulose derivatives which have a good flowability in combination with a reasonably high untapped bulk density and which are also well dispersible in cold water.

Another preferred object of the present invention is to provide a process for producing such cellulose derivatives which does not require the time-consuming steps like drying in an oven or on trays and subsequent grinding as disclosed in British Patent Specification GB 804,306 and in U.S. Pat. No. 2,331,864.

Yet another preferred object of the present invention is to provide a process for producing such cellulose derivatives which does require extruding the cellulose derivatives to strands and cutting the strands as disclosed in WO 96/00748.

Surprisingly, it has been found that the flowability and/or the cold water dispersibility of cellulose derivatives in particulate form can be improved in a novel process for grinding and drying a moist cellulose derivative. Several processes for combined drying and grinding of moist cellulose derivatives are known in the art, such as described in the patent applications GB 2 262 527 A; EP 0 824 107 A2; EP-B 0 370 447 (equivalent to U.S. Pat. No. 4,979,681); EP 1 127 895 A1 (equivalent to US 2001/034441) and EP 0 954 536 A1 (equivalent to U.S. Pat. No. 6,320,043), but none of these references addresses the problem of improving the cold water dispersibility of cellulose derivatives or provide an evidence of good flowability of the cellulose derivatives.

SUMMARY

One aspect of the present invention is a process for producing a particulate cellulose derivative by grinding and drying a moist cellulose derivative, which process comprises the steps of A) providing a cellulose derivative having a moisture content of from 25 to 95 percent, based on the total weight of the moist cellulose derivative, B) grinding and partially drying the moist cellulose derivative in a gas-swept impact mill wherein the gas fed into the impact mill has a temperature of 100° C. or less; and C) contacting the ground and partially dried cellulose derivative with an additional amount of a drying gas outside the gas-swept impact mill, wherein the additional amount of drying gas outside the gas-swept impact mill has a higher temperature than the gas fed into the impact mill.

Another aspect of the present invention is a particulate cellulose derivative producible by the above-mentioned process.

Yet another aspect of the present invention is a method of improving the flowability and/or the cold water dispersibility of a particulate cellulose derivative, which method comprises the steps of A) providing a cellulose derivative having a moisture content of from 25 to 95 percent, based on the total weight of the moist cellulose derivative, B) grinding and partially drying the moist cellulose derivative in a gas-swept impact mill wherein the gas fed into the impact mill has a temperature of 100° C. or less; and C) contacting the ground and partially dried cellulose derivative with an additional amount of a drying gas outside the gas-swept impact mill, wherein the additional amount of drying gas outside the gas-swept impact mill has a higher temperature than the gas fed into the impact mill.

Yet another aspect of the present invention is a particulate cellulose derivative having an untapped bulk density of at least 370 g/l, a Carr Index of 20 or less and a median Equivalent Projected Circle Diameter (EQPC) of at least 200 micrometers.

Yet another aspect of the present invention is an aqueous composition produced by blending water, the above-mentioned particulate cellulose derivative and one or more optional additives.

Yet another aspect of the present invention is a process for the manufacture of capsules which comprises the step of contacting the above-mentioned aqueous composition with dipping pins.

Yet another aspect of the present invention is a process for coating a dosage form which comprises the step of contacting the above-mentioned aqueous composition with the dosage form.

It has been surprisingly found that the way of drying a cellulose derivative in and outside a gas-swept impact mill has a great influence on the flowability and/or the cold water dispersibility of the cellulose derivative. More specifically, it has surprisingly been found that the flowability and/or the cold water dispersibility of a cellulose derivative can be improved if the drying and grinding of a moist cellulose derivative in a gas-swept impact mill is conducted in such a manner that the gas fed into the impact mill has a temperature of 100° C. or less, the cellulose derivative is only partially dried in the gas-swept impact mill and the drying is completed outside the gas-swept impact mill with an additional amount of a drying gas that has a higher temperature than the gas fed into the impact mill.

BRIEF DESCRIPTION OF DRAWINGS

FIG. 1 illustrates a flow sheet of the process of the present invention.

DETAILED DESCRIPTION

The present invention relates to a process for producing a particulate cellulose derivative by drying and grinding a moist cellulose derivative.

The cellulose derivatives used in this process are generally soluble or at least soakable in solvents, preferably water. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the celluloses according to the invention are not limited to these groups.

Examples of cellulose derivatives are hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hm- HPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CMSEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC).

Preferred cellulose derivatives are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. Particularly preferred cellulose derivatives are cellulose ethers having a thermal flocculation point in water, such as, for example, methyl cellulose, methyl hydroxyethyl cellulose, methyl hydroxypropyl cellulose and hydroxypropyl cellulose. The cellulose derivatives are preferably water-soluble, which means that they have a solubility in water of at least 1 gram, more preferably at least 2 grams, most preferably at least 5 grams in 100 grams of distilled water at 25° C. and 1 atmosphere.

Most preferably, the water-soluble cellulose ether is a methylcellulose with a methyl degree of substitution $DS_{methyl}$ of from 1.2 to 2.2, preferably from 1.5 to 2.0; or a hydroxypropyl methylcellulose with a $DS_{methyl}$ of from 0.9 to 2.2, preferably from 1.1 to 2.0, and an $MS_{hydroxypropyl}$ of from 0.02 to 2.0, preferably from 0.1 to 1.2; or a hydroxyethyl methylcellulose with a $DS_{methyl}$ of from 1.15 to 2.3, preferably from 1.15 to 2.2, and an $MS_{hydroxyethyl}$ of from 0.03 to 1.0, preferably from 0.05 to 0.9; or a hydroxyethyl cellulose with an $MS_{hydroxyethyl}$ of from 1.2 to 3.0, preferably from 1.45 to 2.2. The determination of the ether side groups, i.e. the $DS_{methyl}$, $MS_{hydroxyethyl}$ and $MS_{hydroxypropyl}$ can be effected as described by K. L. Ketterer, W. E. Kester, D. L. Wiederrich, and J. A. Grover, Determination of Alkoxyl Substitution in Cellulose Ethers by Zeisel-Gas Chromatographie, Analytical Chemistry, Vol. 51, No. 13, November 1979, 2172-76.

The viscosities of the water-soluble cellulose derivatives can vary over a broad range. In one aspect of the present invention the viscosity of the cellulose derivative is more than 150 mPa·s, preferably from 500 to 200,000 mPa·s, more preferably from 500 to 100,000 mPa·s, most preferably from 1000 to 80,000, particularly from 1000 to 60,000, determined in a 1.5% by weight aqueous solution at 20° C. in a Haake RS600 rheometer with a cone and plate Geometry (CP-60/2°) at 20° C. and at a shear rate of 2.55 s$^{-1}$. In another aspect of the present invention the viscosity of the cellulose derivative is from 1.2 to 200 mPa·s, preferably from 2 to 100 mPa·s, more preferably from 2.5 to 50 mPa·s, in particular from 3 to 30 mPa·s, measured as a 2 weight-% aqueous solution at 20° C. according to ASTM D2363-79 (Reapproved 2006). Such low viscosity cellulose derivatives can be produced in a known manner by partial degradation of higher viscosity cellulose derivatives.

The production of cellulose derivatives, preferably cellulose ethers and cellulose esters, is known in the art. Typically the production process involves activating the cellulose, for example by treatment with an alkali metal hydroxide, reacting the thus treated cellulose with a derivatizing agent, such as an etherifying or esterifying agent, and washing the cellulose derivative to remove by-products. After the washing step the cellulose derivative generally has a moisture content of from 25 to 60 percent, typically from 40 to 55 percent, based on the total weight of the moist cellulose derivative. While the preferred washing liquor may depend on the specific type of cellulose derivative, preferred washing liquors generally are water, isopropanol, acetone, methylethylketone or brine. More preferred washing liquors generally are water or brine. Cellulose derivatives are generally washed at a temperature of from 20 to 120° C., preferably from 65 to 95° C. A solvent-moist, preferably a water-moist filter cake is obtained after washing and separating the cellulose derivative from the washing liquor. The moist cellulose derivative is usually obtained in the shape of moist granules, moist lumps and/or a moist paste.

According to one aspect of the present invention the cellulose derivative has been obtained by separating a cellulose derivative from a suspension thereof in a liquid, such as water, and is subsequently subjected to the process of the present invention. The suspension of particles in a liquid can originate from the production and washing the cellulose derivative, as described above. Separating a cellulose derivative from a suspension can be carried out in a known way, such as centrifugation.

According to another aspect of the present invention a dry cellulose derivative and a liquid, such as water, can be mixed in a compounder to a desired moisture content and the thus obtained moist cellulose derivative is subsequently subjected to the process of the present invention.

It is a great advantage of the process of the present invention that cold water dispersible cellulose derivatives can be obtained without mixing a substantial amount of a surface-treatment additive with the cellulose derivative and a liquid, such as water. Therefore, according to a preferred embodiment of the present invention no substantial amount of a surface-treatment additive is added to the cellulose derivative. By "no substantial amount of a surface-treatment additive" is meant an amount that does not significantly change the surface properties and in particular the cold water dispersibility of the cellulose derivative. Preferably not more than 1 percent, more preferably not more than 0.5 percent, most preferably not more than 0.2 percent, and particularly no amount of a surface-treatment additive is added to the cellulose derivative, based on the dry weight of the cellulose derivative. Surface-treatment additives are, for example, surfactants, such as sorbitol or lauryl sulfates; esters; salts, such as KCl, phosphates, nitrates or sulfates; or sugars, such as lactose, fructose, glucose, sucrose, or maltodextrin; or low molecular weight polymers, such as polyethylene glycols, or propylene glycols. The compounder preferably allows thorough and intense mixing. Useful compounders are, for example, granulators, kneaders, extruders, presses, or roller mills, wherein the mixture of the cellulose derivative and liquid is homogenised by applying shear forces and compounding, such as a twin-screw compounder. Co-rotating as well as counter-rotating machines are suitable. So-called divided trough kneaders with two horizontally arranged agitator blades that engage deeply with one another and that perform a mutual stripping action, as in the case of twin-screw compounders are particularly suitable. Suitable single-shaft, continuous kneaders include the so-called Reflector® compounders, which are high performance mixers of modular construction, consisting of a multi-part, heatable and coolable mixing cylinder and a unilaterally mounted blade mixer (manufacturer: Lipp, Germany). Also suitable are so-called pinned cylinder extruders or Stiftconvert® extruders (manufacturer: Berstorff, Germany). The pins incorporated in the housing serve as abutments in order to prevent the kneaded material rotating together with the shaft. Kneader mixers with so-called double-blade sigma stirrers (manufacturer: Fima, Germany) in a horizontal assembly are particularly suitable. The blades operate at different speeds and their direction of rotation can be reversed. A stirred vessel with a vertically arranged mixer shaft is also suitable if suitable flow baffles are mounted on the vessel wall in order to prevent the kneaded mass rotating together with the stirrer shaft, and in this way an intensive mixing action is imparted to the kneaded material (manufacturer: Bayer AG). Also suitable are double-walled mixing vessels with a planetary stirrer and inline homogeniser.

In step A) of the process and method of the present invention a cellulose derivative is provided that has a moisture content of from 25 to 95 percent, based on the total weight of the moist polysaccharide derivative. Preferred lower limits of the moisture content are 30, and 38 percent respectively. Preferred upper limits of the moisture content are 80, 70 and 60 percent respectively. Most preferably the moisture content is from 40 to 50 percent. The moisture content can be adjusted by addition of a liquid, for example, water, isopropanol, acetone, methylethylketone or brine. Most preferably, water is used. The amount of liquid added to the water-soluble cellulose derivative should be adjusted to the moisture content that the cellulose derivative already has. The moisture content can be determined by ASTM method D-2363-79 (reapproved 1989). The moist cellulose derivative in step A) preferably does not comprise a substantial amount of a surface-treatment additive that is left on the cellulose derivative upon drying of the cellulose derivative, such as the above-mentioned surface-treatment additives. Preferably the cellulose derivative does not comprise more than 1 percent, more preferably not more than 0.5 percent, most preferably not more than 0.2 percent, based on the dry weight of the cellulose derivative, and particularly no amount of a surface-treatment additive. It is to be understood that any residual amounts of by-products from the production of the cellulose derivative, such as sodium hydrochloride, is not encompassed by the term "surface-treatment additive".

The temperature of the cellulose derivative prior to drying and grinding is preferably controlled and optionally varied or adjusted in a range from 5 to 60° C., more preferably from 5 to 45° C., most preferably from 10 to 40° C., and particularly from 10 to 30° C. If a liquid such as water is added to the cellulose derivative prior to drying and grinding, the temperature of the cellulose derivative prior to drying and grinding is preferably controlled and optionally varied or adjusted by controlling and optionally varying or adjusting the temperature of the added liquid and/or the jacket temperature of the compounder.

The cellulose derivative having a moisture content of from 25 to 95 percent is usually in the shape of moist granules, moist lumps and/or a moist paste. In step B) it is subjected to grinding and partially drying in a gas-swept impact mill, preferably an air-swept impact mill, wherein the cellulose derivative is subjected to an impacting and/or shearing stress. Preferred gas-swept impact mills are Ultra Rotor mills (Altenburger Maschinen Jaeckering, Germany) or Turbofiner PLM mills (PALLMANN Maschinenfabrik GmbH & Co. KG, Germany). Gas classifier mills are also useful gas-swept impact mills, for example, the Hosokawa Alpine Air Classifier mill—ZPS Circoplex Hosokawa Micron Ltd., Cheshire, England. Drying is typically accomplished with a combination of gas and mechanical energy. Air or nitrogen gas can be used. In the process of the present invention the gas fed into the impact mill has a temperature of 100° C. or less, preferably of 75° C. or less, more preferably of 50° C. or less. Typically the gas fed into the impact mill has a temperature of 10° C. or more, preferably of 20° C. or more, more preferably of 30° C. or more. A gas stream having the above-mentioned temperature can be created in various ways. In one embodiment of the invention a fresh gas stream having the desired temperature can be fed into the impact mill. In another embodiment of the invention a recycled gas stream having the desired temperature is fed into the impact mill. For example, a gas stream can be separated from the ground and dried cellulose derivative obtained in step C) as described further below, and the resulting solid-free gas stream, or a portion thereof, can be cooled in a cooling system, e.g., using water as coolant. This resulting cooled gas stream can be fed into the mill. Alternatively, the entire amount of cooled gas can be re-heated, e.g. in a natural gas burner. To bring the re-heated gas to the desired temperature for feeding into the impact mill, a separate stream of cold gas can be combined with the hot gas stream before feeding the gas stream into the mill. The gas and the wet product stream are generally fed via separate inlets into the mill, typically gas from the bottom and wet product at a side entrance via a feed screw system connected to the mill. In one aspect of step B) of the process the moist cellulose derivative and a gas are fed into the gas-swept impact mill at a rate of from 38 to 92 $m^3$/kg, more preferably from 55 to 80 $m^3$/kg cellulose derivative, based on the dry weight of cellulose derivative. The circumferential speed of the gas-swept impact mill is preferably not more than 100 m/s. More preferably, the gas-swept impact mill is operated in such a manner that its circumferential speed is in a range from 30 to 100 m/s, most preferably from 35 to 80 m/s.

It is an essential feature of the process of the present invention that in step B) of the process the moist cellulose derivative is ground but only partially dried and in step C) of the process the ground and partially dried cellulose derivative is contacted with an additional amount of a drying gas outside the gas-swept impact mill. Preferably the ratio of the gas flow in the gas-swept impact mill in step B) and the flow of the additional amount of drying gas in step C), i.e. (gas flow in step B)/(additional gas flow in step C) is from 1:10 to 8:1, preferably from 1:5 to 3:1, more preferably from 1:3 to 2:1, most preferably from 1:2 to 1:1. The term "additional amount of a drying gas" as used herein means a drying gas that has not been fed into the gas-swept impact mill. The skilled artisan knows how to achieve only a partial drying in step B). E.g., the gas stream can be determined that would be necessary to essentially dry the cellulose derivative in the gas-swept impact mill at the given process parameters, such as gas temperature and moisture content and temperature of the moist cellulose derivative. Incomplete drying can be achieved in step B), e.g., by feeding a lower amount of gas per unit of cellulose derivative to be ground and dried into the gas-swept impact mill than the amount of gas that would be required to dry and grind the cellulose derivative to an essentially dry product in the gas-swept impact mill. In a preferred aspect of the present invention the gas stream used for drying the cellulose derivative is split into two streams via a slide valve wherein the first gas stream is fed into the gas-swept impact mill and the second gas stream is contacted with the ground and partially dried cellulose derivative that leaves the impact mill. Furthermore, it has been found that a particulate cellulose derivate of improved flowability and/or cold water dispersibility can be obtained if the additional amount of drying gas utilized in step C) outside the gas-swept impact mill (i.e., the second gas stream), has a higher temperature than the gas fed into the impact mill (i.e., the first gas stream). Preferably, the additional amount of drying gas outside the gas-swept impact mill has a temperature that is at least 70° C. higher, more preferably from 100 to 220° C. higher, most preferably from 130 to 180° C. higher than the gas fed into the impact mill.

The first gas stream leaving the impact mill can have a higher or lower temperature than the gas stream fed into the impact mill. The temperature of the first gas stream leaving the impact mill depends on various factors, such as the temperature, amount and moisture content of the moist cellulose derivative and the mechanical energy in the impact mill. The first gas stream leaving the impact mill can be partially or fully separated from the ground and partially dried cellulose derivative before the cellulose derivative is contacted with the second gas stream, but preferably the cellulose derivative is suspended in at least a portion or, more preferably, in the entire amount of the gas stream exiting the gas-swept impact mill when it is contacted with the second gas stream. The amount and the temperature of the second gas stream, i.e. the additional amount of drying gas outside the gas-swept impact mill, is preferably chosen such that the combined gas stream in step C), which is a combination of the first gas stream leaving the impact mill and the additional amount of drying gas utilized in step C), has a temperature which is at least 30° C. higher, more preferably from 30 to 75° C. higher, most preferably from 55 to 75° C. higher, particularly from 55 to 65° C. higher than the temperature of the first gas stream leaving the impact mill. In one aspect of step C) of the process the ground and partially dried cellulose derivative is contacted with an additional amount of drying gas outside the gas-swept impact mill at a rate of from 25 to 200 m$^3$/kg, preferably from 50 to 160 m$^3$/kg cellulose derivative, based on the dry weight of cellulose derivative. The additional amount of drying gas outside the gas-swept impact mill preferably has a temperature of from 80 to 250° C., more preferably from 100 to 220° C., most preferably from 150 to 190° C.

In the drying step C) of the process of the present invention the moisture content of the cellulose derivative is typically reduced to 1 to 20 percent, preferably 1 to 10 percent, more preferably 1 to 5 percent, based on the total weight of the moist cellulose derivative. After step C) the ground and dried cellulose derivative particles are preferably separated from the flow of gas in a separator arranged down-stream the gas-swept impact mill. The separator is preferably designed to conduct gas classification, such as air classification. It can be a centrifugal separator such as, for example, a cyclone, or a filtering separator such as a sifter. Alternatively, depending on the construction of the gas-swept impact mill, a gas classification may already take place in the gas-swept impact mill. The flow of gas that has been separated from the cellulose derivative particles can be recycled and re-used in steps B) and/or C) of the process of the present invention. Alternatively, the flow of gas that has been separated from the cellulose derivative particles is not recycled and not re-used in steps B) and C) of the process of the present invention, but fresh gas from the environment is used in steps B) and/or C).

The above described process is useful for improving the flowability and/or cold water dispersibility of particulate cellulose derivatives.

The particulate cellulose derivative that is produced according to the process of the present invention generally has an untapped bulk density of at least 370 g/l, preferably at least 400 g/l, and more preferably even at least 430 g/l. Untapped bulk densities of up to 600 g/l are generally achieved, or under optimized conditions even up to 650 g/l. Bulk density (BD) as used herein is defined as the ratio of apparent volume to mass of the material taken, called untapped bulk density, and also the ratio of tapped volume to mass of material taken, called tapped bulk density. A useful procedure for measuring these bulk densities is described in United States Pharmacopeia 24, Test 616 "Bulk Density and Tapped Density," United States Pharmacopeia Convention, Inc., Rockville, Md., 1999.

The particulate cellulose derivative that is produced according to the process of the present invention generally has a Carr index of 20 or less, preferably of 16 or less, more preferably of 13 or less, most preferably of 12 or less. Under optimized conditions, e.g. by subjecting the ground and dried cellulose derivative after step C) to sieving as described further below, particulate cellulose derivatives can be obtained that have a Carr index of 10 or less, or even a Carr index of 6 or less. The minimum Carr index is 1. The Carr index C is an indication of the compressibility of a powder. It is calculated by the formula $$C=100*(BD\ tapped-BD\ untapped)/BD\ tapped,$$

wherein "BD tapped" is the tapped bulk density of a powder and "BD untapped" is the untapped bulk density of a powder. The Carr index is frequently used in the pharmaceutical science as an indication of the flowability of a powder. A Carr index below 15 is considered to be an indication of good flowability. (Kanig, Joseph L.; Lachman, Leon; Lieberman, Herbert A. (1986). *The Theory and Practice of Industrial Pharmacy* (3 ed.). Philadelphia: Lea & Febiger.)

The particulate cellulose derivative that is produced according to the process of the present invention has a good dispersibility in cold water. By "cold water" is meant water below, at or only slightly above room temperature, i.e., water at a temperature of generally 0 to 40° C., typically 5 to 30° C., more typically 10 to 25° C. The dispersibility in cold water is determined as described in the examples. A criterion for poor or no cold water dispersibility is visible by lump formation of the cellulose derivative in cold water. The lump formation strongly hinders the dissolution of the product over time.

Moreover, the process of the present invention is useful for producing cellulose derivatives of a certain size and shape. Particle size and shape of a particulate cellulose derivative can be determined by a high speed image analysis method which combines particle size and shape analysis of sample images. An image analysis method for complex powders is described in: W. Witt, U. Köhler, J. List, Current Limits of Particle Size and Shape Analysis with High Speed Image Analysis, PARTEC 2007. A high speed image analysis system is commercially available from Sympatec GmbH, Clausthal-Zellerfeld, Germany as dynamic image analysis (DIA) system QICPIC™. The high speed image analysis system is useful for measuring among others the following dimensional parameters of particles:

EQPC:

EQPC of a particle is defined as the diameter of a circle that has the same area as the projection area of the particle. For the purpose of the present invention the median EQPC is the volume distribution average of all particles in a given sample of a particulate cellulose derivative. The median EQPC means that 50% of the EQPC of the particle distribution is smaller than the given value in µm and 50% is larger.

LEFI:

The particle length LEFI is defined as the longest direct path that connects the ends of the particle within the contour of the particle. "Direct" means without loops or branches. For the purpose of the present invention the median LEFI is the volume distribution average of all particles in a given sample of a particulate cellulose derivative. The median LEFI means that 50% of the LEFI of the particle distribution is smaller than the given value in µm and 50% is larger.

The particulate cellulose derivative that is produced according to the process of the present invention generally has a median Equivalent Projected Circle Diameter (EQPC) of at least 200 micrometers, preferably of at least 220 micrometers, more preferably of at least 240 micrometers. The particulate cellulose derivative generally has a median EQPC of up to 700 micrometers, preferably up to 600 micrometers, more preferably up to 500 micrometers.

The particulate cellulose derivative that is produced according to the process of the present invention generally has a median LEFI of from 400 to 1200 micrometers, more preferably from 420 to 1100 micrometers, most preferably from 450 to 1000 micrometers.

In an optional step D) of the process of the present invention the ground and dried cellulose derivative can be sieved through a sieve of from 125 to 400, preferably from 160 to 355, more preferably from 180 to 315, and most preferably from 200 to 300 micrometers mesh size, for example a sieve of 220 µm mesh size. The optional sieving step can be conducted after having separated the ground and dried cellulose derivative from the flow of gas in a separator arranged downstream the gas-swept impact mill, such as a cyclone. Useful sieves are known in the art and described in DIN 4188. A fine fraction having a particle size below the mesh size of the sieve and a coarse fraction having a particle size above the mesh size of the sieve is obtained. These two fractions can be used separately as final products according to the invention, showing cold water dispersibility for both the fine fraction as well as for the coarse fraction. Alternatively, in the process of the present invention the ground and dried cellulose derivative is not sieved through a sieve. According to the process of the present invention cold water dispersible cellulose derivatives are producible regardless whether the ground and dried cellulose derivative is sieved or not. The entire amount of ground and dried cellulose derivative is water dispersible. This is a great advantage since the entire amount of ground and dried cellulose derivative is useful and no amount needs to be recycled to the drying and grinding process or used for other purposes where cold water dispersibility is of less importance.

A preferred embodiment of carrying out the process of the present invention is illustrated by FIG. 1 which is described in more detail below, but which is not to be construed to limit the scope of the present invention to the embodiment of the invention illustrated by FIG. 1. A blower 11 circulates air or preferably nitrogen through a mill circuit, providing a total gas stream 1 of preferably 1000-2200 m³/h measured by a flow meter. After the blower 11 the total gas stream 1 can be split into a cooled gas stream 4 and a gas stream through a burner 12. This heated gas stream 5 after the burner can be split into a gas stream 3 through a gas swept impact mill 14 and into a gas stream through a bypass 2, which serves as an additional amount of a drying gas outside the gas-swept impact mill. The moisturized cellulose derivative ("moisturized CE") can be added through a feed screw system 13 into the gas swept impact mill 14. The temperature 6 of the gas stream 3 before the gas swept impact mill is measured. The temperature of the gas stream 7 after the gas swept impact mill is measured as well. After the junction of the gas stream through the bypass 2 and the gas stream 3 through the gas swept impact mill, the temperature of the combined gas stream 8 containing the ground cellulose derivative is measured. The conduit after the mill till the beginning of a cyclone 15 can be considered as flash dryer. The combined gas stream 8 is fed to the cyclone 15 where substantially the entire amount of cellulose derivative, except some residual amount of fine particles (dust) is separated from the gas stream. The residual amount of dust is removed in a filter 16. The temperature of the total gas stream 9 is measured after it has left the cyclone 15 and before it enters the filter 16. The filtered gas stream is passed through a washer/cooler 17. The temperature 10 of the washed and cooled gas stream is measured; the washed and cooled gas stream corresponds to the total gas stream 1 that is circulated by the blower 11.

The present invention further relates to a particulate cellulose derivative having i) an untapped bulk density of at least 370 g/l, preferably at least 400 g/l, and more preferably at least 430 g/l, ii) a Carr Index of 20 or less, preferably of 16 or less, more preferably of 13 or less, most preferably of 12 or less, and under optimized production conditions, a Carr index of 10 or less, or even a Carr index of 6 or less, and iii) a median EQPC of at least 200 micrometers, preferably of at least 220 micrometers, more preferably of at least 240 micrometers.

The particulate cellulose derivative of the present invention generally has an untapped bulk density of up to 600 g/l, or under optimized conditions even up to 650 g/l. The minimum Carr index is 1. The particulate cellulose derivative of the present invention generally has a median EQPC of up to 700 micrometers, preferably up to 600 micrometers, more preferably up to 500 micrometers. The particulate cellulose derivative of the present invention generally has a median LEFI of from 400 to 1200 micrometers, more preferably from 420 to 1100 micrometers, most preferably from 450 to 1000 micrometers.

Moreover, the particulate cellulose derivative of the present invention preferably has a particle size such that at least 60 weight percent, preferably at least 75 weight percent, more preferably at least 85 weight percent, most preferably at least 95 weight percent, and particularly at least 99 weight percent of the cellulose derivative particles are retained on a sieve of 160 micrometers mesh size, preferably on a sieve of 170 micrometers mesh size, more preferably on a sieve of 180 micrometers mesh size, most preferably on a sieve of 200 micrometers mesh size, and particularly on a sieve of 220 micrometers mesh size and pass through a sieve of 1250 micrometers mesh size (sieves of DIN No. 4188), preferably through a sieve of 1000 micrometers mesh size, more preferably through a sieve of 800 micrometers mesh size, and most preferably through a sieve of 630 micrometers mesh size.

The particulate cellulose derivative that is produced according to the process of the present invention and the novel particulate cellulose derivative of the present invention are useful in a variety of applications, where good dispersibility of the particulate cellulose derivative in cold water is beneficial. For example, the particulate cellulose derivative is useful in pharmaceutical applications, preferably in liquid suspensions comprising a cellulose derivative and a medicament, or in aqueous solutions of the particulate cellulose derivative for the preparation of hard shell capsules.

Another aspect of the present invention is an aqueous composition which has been produced by blending water, the particulate cellulose derivative of the present invention and one or more optional additives. Preferably water, the particulate cellulose derivative of the present invention and one or more optional additives are blended in such an amount such that the composition preferably comprises from 5 to 40 percent, more preferably from 10 to 30 percent, of the cellulose derivative of the present invention, based on the total weight of the aqueous composition. This aqueous composition is particularly useful for the manufacture of capsules or coatings of dosage forms. The cellulose derivative preferably has a viscosity of from 2 to 200 mPa·s, more preferably from 2 to 100 mPa·s, most preferably from 2.5 to 50 mPa·s, in particular from 3 to 30 mPa·s, determined in a 2% by weight aqueous solution at 20° C. according to ASTM D2363-79 (Reapproved 2006). Optional additives may be incorporated in the composition, such as coloring agents, flavor and taste improvers, antioxidants, plasticizers, and surfactants. For example, when producing capsules a water-soluble food dye, such as red oxide, or a natural dye, may be used as a coloring agent; $TiO_2$ may be used as a masking agent; polyethylene glycol, polypropylene glycol, sorbitol or glycerin may be used as a plasticizer or as a surfactant to improve the flexibility of the capsule film. Particularly useful additives for coatings of solid forms are single layer film plasticizers, solids-loading enhancers, a second cellulose derivative, preferably a second cellulose ether, surfactants, lubricants, polishing agents, pigments, anti-tack agents, glidants, opacifiers, coloring agents and any combination thereof.

In one aspect of the present invention, the aqueous composition may be used for coating dosage forms, such as tablets, granules, pellets, caplets, lozenges, suppositories, pessaries or implantable dosage forms, to form a coated composition. Preferred dosage forms are pharmaceutical dosage forms, nutrition supplements or agricultural dosage forms.

In another aspect of the present invention the aqueous composition may be used for the manufacture of capsules. One method for the manufacture of capsules is the "hot-pin method". This method preferably comprises the steps of (a) providing the above-mentioned aqueous composition, (b) pre-heating dipping pins so that they are at a temperature above the gelation temperature of the aqueous composition when dipped into the aqueous composition, (c) dipping the pre-heated dipping pins into the aqueous composition maintained at a temperature below its gelation temperature, (d) withdrawing the dipping pins from the aqueous composition obtaining a film on the dipping pins, and (e) drying the film on the dipping pins at a temperature above the gelation temperature of the aqueous composition so as to obtain molded capsule shells on the pins. The hot-pin method used to prepare capsules from the aqueous composition of the cellulose ether is described in detail in the International Patent Publication No. WO 2008/050209.

Another method for the manufacture of capsules is the "cold-pin method". In this method the above-mentioned aqueous composition additionally comprises a gelling agent such as carrageenan, pectin, gellan gum, or another sequestering agent or gelling aid, such as potassium, magnesium, ammonium, or calcium ions. In the cold-pin method pins are generally kept at room temperature and are dipped into the aqueous composition maintained at a temperature above its gelation temperature, preferably at a temperature of 45 to 60° C., the dipping pins are withdrawn from the aqueous composition and a film is obtained on the dipping pins, and the film is dried on the dipping pins to obtain molded capsule shells on the pins. The cold-pin method used to prepare capsules from the above-mentioned aqueous composition is described in detail in European Patent Application No. EP 0 714 656 and in U.S. Pat. No. 6,410,050.

The present invention is further illustrated by the following Examples which are not to be construed to limit the scope of the invention. Unless otherwise indicated, all parts and percentages are by weight.

Examples 1-5

A commercially available continuous compounder with heating and cooling jacket was used to add water to dry METHOCEL™ E 5 Premium LV cellulose ether. The compounder jacket was supplied with a fluid of −10° C. to −8° C. The fluid in the compounder jacket was used to adapt the temperature of the cellulose ether prior to drying and grinding to about 17-24° C., but the temperature of the cellulose ether was measured separately and usually did not reach the temperature of the fluid in the compounder jacket because the water used for the hydration of the cellulose ether in the compounder was only at about 5°.

The cellulose ether which was used in Examples 1-5 as a starting material had an untapped bulk density of 370 g/l, a tapped bulk density of 521 g/l, a Carr Index of 31, a median Equivalent Projected Circle Diameter (EQPC) of 83 micrometers and an median particle length LEFI of 240 micrometers. The cellulose ether used in Examples 1-5 was METHOCEL™ E 5 Premium LV cellulose ether which is commercially available from The Dow Chemical Company. METHOCEL™ E 5 Premium LV cellulose ether has a degree of substitution of methoxyl groups of 28.0-30.0% and of hydroxypropyl groups of 7.0-12.0%, and a viscosity of 5 mPa·s, measured as a 2 percent aqueous solution at 20° C. METHOCEL™ E 5 Premium LV having a moisture content of less than 3%, based on the total weight of the moist cellulose ether, was fed continuously at a feed rate of 20 kg/h into the compounder. Water of a temperature of 5° C. was continuously added to the compounder. The wet product was transported continuously via a transport belt into a mill feed unit (Altenburger Maschinen Jaeckering GmbH, Hamm, Germany). The bottom blades of the vessel agitator pressed the paste into a single augur screw mounted at the bottom of the vessel. The wet product was forced through a perforated plate directly into the side of an Ultrarotor II "S" impact mill (Altenburger Maschinen Jaeckering GmbH, Hamm, Germany) between the first and second grinding stage. The mill was equipped with seven grinding stages. The bottom five grinding stages were equipped with standard grinding bars. No grinding bars were installed in the top two grinding stages. The interior of mill jacket had the standard Altenburger corrugated stationary grinding plates.

The rotor of the impact mill was operated at a circumferential speed of 58 m/s. A specific gas flow system used herein was a closed loop system applying nitrogen as gas. The gas flow system was composed of three separately controllable gas streams. The control operation was carried out by slide valves allowing controlling the amount of the respective gas stream. At the same time the temperature of the gas streams could be controlled via a natural gas burner and a gas cooling system using cold water as coolant. The resulting gas temperatures of the respective gas streams are listed in Table 1 below.

A preferred flow of the gas streams is described hereafter with reference to FIG. 1, but it should be noted that the present invention is not limited to this embodiment of the invention. A total gas stream 1 of 2000 to 2330 m³/h was partly blown into a natural gas burner 12. Before the junction point of the cold gas and the hot gas, the hot gas can be divided into two separate streams of the same temperature. One of these separate gas streams of about 1000 m³/h was sent around the impact mill as by-pass 2, which served as an additional amount of a drying gas outside the gas-swept impact mill. The other gas stream was sent to the junction point with the cooled gas stream to enter the impact mill from the bottom of the mill. For Examples 3-5 only a cooled gas stream 4 of about 1000 m³/h was fed into the mill. For Examples 1-2 about 1300 m³/h hot gas were fed into the mill. No cooled gas was mixed to this hot gas. After the milling in the gas swept impact mill 14, the gas stream 2 through the bypass and the gas stream 3 through the impact mill were combined. The solid material leaving the mill together with the combined gas streams was separated via a cyclone 15 and the resulting solid-free gas stream 9 was passed through a filter 16 and subsequently cooled in a washer/cooler 17 using water as coolant. The resulting cool total gas stream 1 was sent to a blower 11. For Examples 1-3 the cooled gas 4 leaving the blower 11 was fed into the gas swept impact mill 14. Alternatively, the cooled gas stream can be sent completely back to the natural gas burner 12 and heated up again. Impact milling and drying operation with no cooled gas usage was applied in Examples 1-2. Thus the gas flow system allowed running the drying and grinding of the cellulose derivative with or without the addition of cooled gas into the mill. The cellulose ethers were directly collected after the cyclone 15 by sieving through an Algaier tumbler screening machine (Allgaier, Uhingen, Germany) equipped with a 220 μm sieve. The final product moisture was smaller than 1.4-2.4% by weight.

The tapped and untapped bulk density of the cellulose derivative in particulate form was measured using a Hosokawa Powder Characteristics Tester: Model PT-N available from Hosokawa Micron, Osaka Japan.

The median LEFI and the median EQPC are the volume distribution average of the LEFIs and EQPCs of all particles in a given sample of a particulate cellulose derivative, which were measured by an image analyzer (high speed image analyzer sensor QICPIC, Sympatec, Germany, with dry disperser RODOS/L with an inner diameter of 4 mm and dry feeder VIBRI/L and Software WINDOX5, Vers. 5.3.0 and M7 lens)

The dispersibility in cold water (CWD) and torque build-up reflecting viscosity build-up of the particulate cellulose derivatives after 60 minutes were determined according to the following procedure: A jacketed glass vessel of 250 ml was filled with 125 ml of tap water of 20° C. The jacket of the vessel was kept at 20° C. by a thermostat. A torque measurement agitator device (Haake VT 550, Thermo Scientific, Karlsruhe, Germany) carrying an agitator being equipped with two rectangular blades, each one perforated with a 8 mm hole, was used for the measurement. The agitator blades were mounted on opposite sides with a 10 degree pitch against the axis, fully covered with the liquid in the vessel, having a distance from the vessel wall of 5 mm. The agitator was turned on to 250 rpm. 10% by weight of cellulose ether were dosed in one batch into the vessel containing the water while agitating constantly. A criterion for poor cold water dispersibility was visible by lump formation of the cellulose ether in cold water causing irregular torque peaks. The lump formation strongly hinders the dissolution of the cellulose derivative over time.

The conditions of the process of the present invention and the properties of the produced particulate cellulose derivatives are listed in Table 1 below. Example 1 is a Comparative Example but is not prior art. In all Examples and Comparative Examples the cellulose derivatives are cellulose ethers (CE).

TABLE 1

| No. in FIG. 1 | | (Comparative) Example | | | | |
|---|---|---|---|---|---|---|
| | | 1* | 2 | 3 | 4 | 5 |
| | CE Moisture before grinding, based on moist CE [%] | 44 | 44 | 46 | 46 | 46 |
| | CE Temperature before grinding [° C.] | 20 | 20 | 17 | 17 | 17 |
| | Water Temperature [° C.] | 4.9 | 4.9 | 5.7 | 5.7 | 5.7 |
| 1 | Total gas stream [m³/h] | 2326 | 2326 | 2006 | 2006 | 2006 |
| 2 | Gas stream through by-pass [m³/h] | 1029 | 1029 | 998 | 998 | 998 |
| 3 | Gas stream through mill [m³/h] | 1297 | 1297 | 1008 | 1008 | 1008 |
| | Ratio gas stream through mill/through by-pass [m³/h] | 1.3/1 | 1.3/1 | 1/1 | 1/1 | 1/1 |
| 4 | Cooled gas flow [m³/h] | 0 | 0 | 1000 | 1000 | 1000 |
| | Tip speed [m/s] | 57.8 | 57.8 | 57.8 | 57.8 | 57.8 |
| 5 | Gas temperature after burner [° C.] | 102 | 102 | 187 | 187 | 187 |
| 6 | Temp. gas stream before mill [° C.] | 102 | 102 | 30 | 30 | 30 |
| 2 | Temp. gas through by-pass | 102 | 102 | 187 | 187 | 187 |
| | Difference between temp. in by-pass 2 and in gas stream 6 before mill | 0 | 0 | 157 | 157 | 157 |
| 7 | Temp. gas stream after mill [° C.] | 83 | 83 | 53 | 53 | 53 |
| 8 | Temp. of combined gas streams [° C.] | 95 | 95 | 106 | 106 | 106 |
| 9 | Temp. gas stream before filter [° C.] | 89 | 89 | 103 | 103 | 103 |
| 10 | Temp. gas stream before blower [° C.] | 29 | 29 | 31 | 31 | 31 |
| | Sieved through 220 μm sieve | Yes | Yes | Yes | Yes | No |
| | Fraction | Fine 73% | Coarse 27% | Fine 56% | Coarse 44% | 100% |
| | Cold Water Dispersible | no | yes | yes | yes | yes |
| | Median EQPC [μm] | 174 | 300 | 176 | 468 | 263 |
| | Median LEFI [μm] | 252 | 444 | 275 | 925 | 485 |
| | BD untapped [g/l] | 448 | 446 | 462 | 473 | 512 |
| | BD tapped [g/l] | 523 | 516 | 551 | 502 | 578 |
| | Carr Index | 14.3 | 13.6 | 16.2 | 5.8 | 11.4 |

*Comparative, but not prior art

When determining the dispersibility in cold water, the cellulose ether of Example 1 (comparative) was still not dissolved after 60 min. The cellulose ether of Example 1 showed strong torque peaks caused by lump formation.

In contrast, no lump formation could be detected for Examples 2-5. The cellulose ethers were fully dissolved already after 30 minutes, showing a constant torque and viscosity.

Example 2 illustrates that cold water dispersible cellulose derivatives of the present invention can be achieved without applying the process of the present invention, but in this case the ground and dried cellulose derivative has to be sieved through a sieve of from 125 to 400, preferably from 160 to 355, more preferably from 180 to 315, and most preferably from 200 to 300 micrometers mesh size and only a portion of the cellulose derivative is cold water dispersible. Examples 3-5 illustrate that according to the process of the present invention cold water dispersible cellulose derivatives of the present invention can be achieved regardless whether the ground and dried cellulose derivative is sieved or not. The entire amount of ground and dried cellulose derivative is water dispersible. This is a great advantage since the entire amount of ground and dried cellulose derivative is useful and no amount needs to be recycled to the drying and grinding process or used for other purposes where cold water dispersibility is of less importance.

Example 4 illustrates that even a lower Carr Index (i.e., even a better flowability) can be achieved if the ground and dried cellulose derivative is subjected to the optional sieving step D) as described above.

What is claimed is:

1. A process for producing a particulate cellulose derivative comprising the steps of
   A) providing a moist cellulose derivative having a moisture content of from 25 to 95 percent, based on the total weight of the moist cellulose derivative, with the proviso that no substantial amount of a surface-treatment additive is added to the cellulose derivative,
   B) grinding and partially drying the moist cellulose derivative in a gas-swept impact mill wherein a gas fed into the impact mill has a temperature of 100° C. or less; and
   C) contacting the ground and partially dried cellulose derivative with an additional amount of a drying gas outside the gas-swept impact mill, wherein the additional amount of drying gas outside the gas-swept impact mill has a higher temperature than the gas fed into the impact mill
   to produce the particulate cellulose derivative.

2. The process of claim 1 wherein the additional amount of drying gas outside the gas-swept impact mill has a temperature that is at least 70° C. higher than the gas fed into the impact mill.

3. The process of claim 1 wherein the ratio of the gas flow in the gas-swept impact mill in step B) and the flow of the additional amount of drying gas in step C) is from 1:10 to 8:1.

4. The process of claim 1 wherein the circumferential speed of the gas-swept impact mill is not more than 100 m/s.

5. The process of claim 1 wherein in a step D) the ground and dried cellulose derivative is sieved through a sieve of from 125 to 400 micrometers mesh size and the cellulose derivative retained on the sieve is recovered.

6. The process of claim 1 wherein the cellulose derivative is a cellulose ether.

7. The process of claim 1 wherein the produced particulate cellulose derivative has an untapped bulk density of at least 370 g/l or a Carr Index of 20 or less or both.

8. A particulate cellulose derivative producible by the process of claim 1.

9. A method of improving the flowability and/or the cold water dispersibility of a particulate cellulose derivative comprising the steps of
   A) providing a moist cellulose derivative having a moisture content of from 25 to 95 percent, based on the total weight of the moist cellulose derivative, with the proviso that no substantial amount of a surface-treatment additive is added to the cellulose derivative,
   B) grinding and partially drying the moist cellulose derivative in a gas-swept impact mill wherein a gas fed into the impact mill has a temperature of 100° C. or less; and
   C) contacting the ground and partially dried cellulose derivative with an additional amount of a drying gas outside the gas-swept impact mill, wherein the additional amount of drying gas outside the gas-swept impact mill has a higher temperature than the gas fed into the impact mill.

10. A particulate cellulose derivative having an untapped bulk density of at least 370 g/l, a Carr Index of 20 or less, a median Equivalent Projected Circle Diameter (EQPC) of at least 200 micrometers and a viscosity of from 1.2 to 200 mPa·s, measured as a 2% by weight aqueous solution at 20° C., with the proviso that the particulate cellulose derivative does not comprise a substantial amount of a surface-treatement additive.

11. The particulate cellulose derivative of claim 10 having a Carr Index 13 or less.

12. The process of claim 2 wherein the circumferential speed of the gas-swept impact mill is not more than 100 m/s.

* * * * *